United States Patent
Zwiener et al.

(10) Patent No.: US 9,216,222 B2
(45) Date of Patent: Dec. 22, 2015

(54) ISOAMYL NITRITE FORMULATIONS

(71) Applicant: Southwest Research Institute, San Antonio, TX (US)

(72) Inventors: Albert M. Zwiener, Helotes, TX (US); Kenneth H. Carson, San Antonio, TX (US); Joseph A. McDonough, Helotes, TX (US); Larry A. Cabell, San Antonio, TX (US); Norma L. Cantu, San Antonio, TX (US); Sandra J. Drabik, San Antonio, TX (US); Andrew P-Z. Clark, San Antonio, TX (US); Paul M. Thompson, San Antonio, TX (US); Richard Michael Corbett, Dresher, PA (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 0 days.

(21) Appl. No.: 14/054,135

(22) Filed: Oct. 15, 2013

(65) Prior Publication Data

US 2015/0105474 A1    Apr. 16, 2015

(51) Int. Cl.
*A61K 47/06* (2006.01)
*A61K 31/04* (2006.01)
*A61K 9/00* (2006.01)
*A61K 47/44* (2006.01)

(52) U.S. Cl.
CPC ............... *A61K 47/06* (2013.01); *A61K 9/0043* (2013.01); *A61K 31/04* (2013.01); *A61K 47/44* (2013.01)

(58) Field of Classification Search
CPC ...................................................... A61K 47/06
See application file for complete search history.

(56) References Cited

U.S. PATENT DOCUMENTS

| | | | |
|---|---|---|---|
| 2,927,939 A | 3/1960 | Yunker, Jr. et al. | |
| 3,106,511 A | 10/1963 | Cuttler et al. | |
| 4,309,303 A | 1/1982 | Boyce | |
| 5,646,181 A * | 7/1997 | Fung et al. | 514/506 |
| 8,987,496 B1 | 3/2015 | McDonough et al. | |
| 2003/0149292 A1 | 8/2003 | Karrer et al. | |
| 2009/0326638 A1 * | 12/2009 | Atanasoska et al. | 623/1.15 |

OTHER PUBLICATIONS

S.I. Baskin, et al, "Cyanide Poisoning", Medical Aspects of Chemical and Biological Warfare, Walter Reed Army Medical Center, Washington, D.C., 1997, Chapter 10, pp. 271-286.

K. Mathes, et al, "The Determination of Methaemoblobin and Cyanomethaemoglobin in Circulating Blood", Naunyn-Schmiedebergs Arch. Exp. Pathol. Pharmakol., 1939, 191; pp. 706-714 (English translation not available).

* cited by examiner

*Primary Examiner* — Wu-Cheng Winston Shen
*Assistant Examiner* — Christopher R Stone
(74) *Attorney, Agent, or Firm* — Grossman, Tucker et al

(57) ABSTRACT

The present invention is directed at isoamyl nitrite formulations suitable for use in medicinal applications. The formulations include a composition of isoamyl nitrite in combination with an epoxidized vegetable oil, identified as stabilized isoamyl nitrite. The isoamyl nitrite may also be combined with petrolatum. Methods of treatment of the formulations are applicable to cyanide poisoning, $H_2S$ poisoning as well as treatment for elevated blood pressure.

17 Claims, 6 Drawing Sheets

ISOAMYL NITRITE FORMULATIONS

GOVERNMENT FUNDING

This invention was made with United States Government support under Contract No. HHSO100201100038C awarded by the Department of Health and Human Services, Assistant Secretary for Preparedness and Readiness, Office of Acquisitions Management, Contracts and Grants. The Government has certain rights in this invention.

FIELD OF THE INVENTION

This disclosure relates to isoamyl nitrite formulations that can be employed in medicinal applications such as an antidote for cyanide and/or hydrogen sulfide poisoning as well as high blood pressure.

BACKGROUND

Amyl nitrite ($C_5H_{11}ONO$) is a known vasodilator and is therefore employed to treat heart disease and angina. In addition, amyl nitrite is used as an antidote for cyanide poisoning where it acts as an oxidant to induce the formation of methemogloblin which in turn can attenuate cyanide as cyanomethemoglobin. The alkyl group is generally unreactive and the chemical and biological properties are primarily due to the nitrite (ONO) group.

U.S. Pat. No. 3,106,511 relates to medicament compositions containing amyl nitrite and to their preparation and use. U.S. Pat. No. 4,309,303 relates to a method of stabilizing liquid alkyl nitrites by adding ethyl hydroxyethyl cellulose, calcium silicate and mixtures thereof and mixing to produce solid state compositions and to stabilize compositions thereof. U.S. Patent Publication No. 2003/0149292 relates to the continuous synthesis of alkyl nitrites by reacting an alcohol with an inorganic nitrite in an acidic medium.

Despite previous uses, amyl nitrite's utility as a field antidote treatment is limited by its stability characteristics (presently 2 year storage at 2-8° C. and limited storage at 25° C.). In addition, amyl nitrite is administered by nasal inhalation, which makes it difficult to determine dose level and the amount of amyl nitrite that is delivered (as measured by blood methemogloblin concentration). Additionally, due to unknown dose quantity delivered, no relationships have been established between dose and efficacy or dose and safety.

It is also useful to note that amyl nitrite is a relatively low viscosity and volatile fluid with a boiling point of 97-99° C. As noted, it is typically employed in drug form by inhalation of vapors of the liquid. Accordingly, the relatively high volatility can reduce the efficacy of a dose through evaporation away from the target zone and/or uncontrolled release.

SUMMARY

The present invention relates to isoamyl nitrite formulations that may be employed in medicinal applications such as an antidote for cyanide and/or hydrogen sulfide poisoning as well as high blood pressure. A formulation identified as stabilized isoamyl nitrite (SIAN) herein comprises a mixture of isoamyl nitrite with an epoxidized vegetable oil. The epoxidized vegetable oil may be present at a level of 1.0-10.0% by weight and the isoamyl nitrite is present at a level of 99.0-90.0% by weight.

The present invention also relates to an isoamyl nitrite formulation that comprises a mixture of isoamyl nitrite with petrolatum. The petrolatum may comprise a hydrocarbon mixture of 16-32 carbon atoms having a melting point range of 35-55° C. and a specific gravity of 0.80-0.90. The isoamyl nitrite utilized in such mixture may comprise the stabilized isoamyl nitrite noted above. Optionally, one may include fumed silica in such formulation.

The present invention also relates to the preparation of an isomerically pure isoamyl nitrite or 3-methylbutyl nitrite via reaction of isomerically pure isoamyl alcohol (3-methylbutanol) with nitrous acid, wherein the nitrous acid is formed in situ by reaction of sulfuric acid with sodium nitrite in water. This is then followed by seeding the reaction with an inorganic salt to control the temperature in the range of -5.0 to 2.0° C. during sulfuric acid addition. Isomerically pure isoamyl nitrite is then recovered at a purity level of 90.0% by weight or more.

The present invention also relates to the formation of nitrite terminated aliphatic polyethers. Isoamyl nitrite may therefore be combined with a hydroxy terminated polyether to convert one or both of the hydroxyl groups into nitrite functionality.

The present invention also relates to mixtures of isoamyl nitrite with hydroxyl-terminated polysiloxane type polymers. The hydroxyl-terminated polysiloxane polymers include polydimethylsiloxane (PDMS) which has a viscosity in the range of 5000-20,000 cP. Such formulation may optionally include fumed silica.

The present invention also relates to a nasal instillation method for delivery of any one of the above isoamyl nitrite formulations for therapeutic effect. A positive displacement micropipette equipped with a piston tip ensures that any one of the formulations may be accurately delivered to a given patient.

FIGURES

The above mentioned and other features of this disclosure, and the manner of attaining them, will become more apparent and better understood by reference to the following description of embodiments described herein, taken in conjunction with the accompanying drawings, wherein.

DETAILED DESCRIPTION

Figure 1:
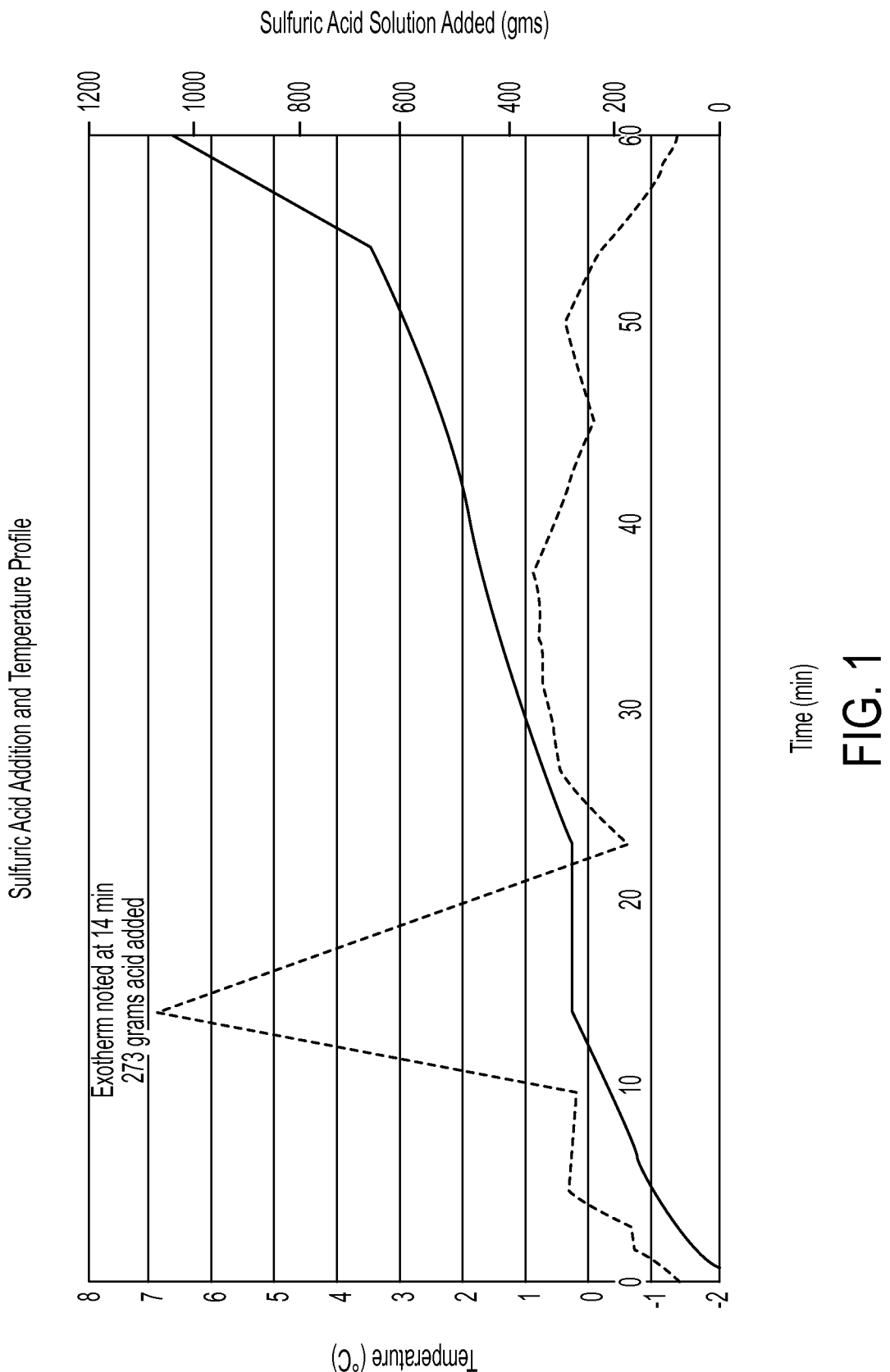
FIG. 1 illustrates a temperature profile of isoamyl nitrite synthesis with an uncontrolled exothermic precipitation of sodium sulfate.

It may be appreciated that the present disclosure is not limited in its application to the details of construction and arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

As noted, the present disclosure provides for the preparation of isoamyl nitrite formulations which can be used for medicinal applications. Preferably, the amyl nitrite that is employed herein is a relatively high purity isoamyl nitrite or $(CH_3)_2CHCH_2CH_2ONO$. Such isomerically pure isoamyl nitrite, otherwise known as 3-methylbutyl nitrite, may be present in a mixture with any other isomers of amyl nitrite at a level of at least 90% by weight or more. Accordingly, the level of isoamyl nitrite in mixture with other isomers of amyl nitrite can be 90-100% by weight. When present at 100% by weight, the isoamyl nitrite comprises only 3-methylbutyl nitrite.

The isoamyl nitrite herein is preferably produced at the indicated purity by reacting isoamyl alcohol with nitrous acid, wherein the nitrous acid is formed in situ by the addition of an inorganic acid such as sulfuric acid with sodium nitrite in water. This is then followed by seeding the reaction with an inorganic salt such as sodium sulfate, where the temperature of the reaction is maintained in the range of −5° C. to 2° C. during the addition of the sulfuric acid. This may be summarized as follows:

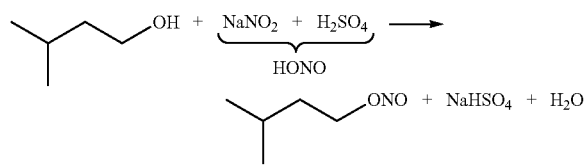

More specifically, the above process to prepare isoamyl nitrite preferably comprises the addition of one molar equivalent of sulfuric acid as a 60 wt % solution to a cooled (−5° C. to 2° C.) mixture of isoamyl alcohol and 17 wt % sodium nitrite while keeping the temperature between −5° C. to 2° C. Maintaining this temperature range throughout the sulfuric acid addition is important, because operating at higher temperature may lead to elevated impurity levels in the product, isoamyl nitrite. As the sulfuric acid addition proceeds, the reaction by-product, sodium sulfate, accumulates in solution. If precipitation of sodium sulfate is not controlled, the solution concentration of sodium sulfate may reach supersaturation, leading to an uncontrolled, exothermic precipitation, with a concomitant temperature spike, leading to batch temperatures as high as 10° C. At such temperatures, the yield of the product isoamyl nitrite decreases and an increase in impurities may be observed, including the primary impurity, isoamyl alcohol.

To prevent an uncontrolled temperature spike, a seeding protocol is employed that involves charging with an inorganic salt such as sodium sulfate decahydrate ($Na_2SO_4 \cdot 10H_2O$) to cause sodium sulfate formed in the reaction to precipitate. Preferably, seeding sodium sulfate decahydrate (equal to 1% of the reaction by-product of sodium sulfate formed) after the addition of 5-10% of the sulfuric acid led to controlled precipitation. As the remainder of sulfuric acid is added, sodium sulfate precipitates as it is formed. Therefore, the exotherm associated with the precipitation occurs over the course of the entire addition of sulfuric acid, making it possible to control the temperature through active cooling with no large temperature spikes. Batch temperatures are therefore maintained at temperatures less than or equal to 2° C.

Figure 2:
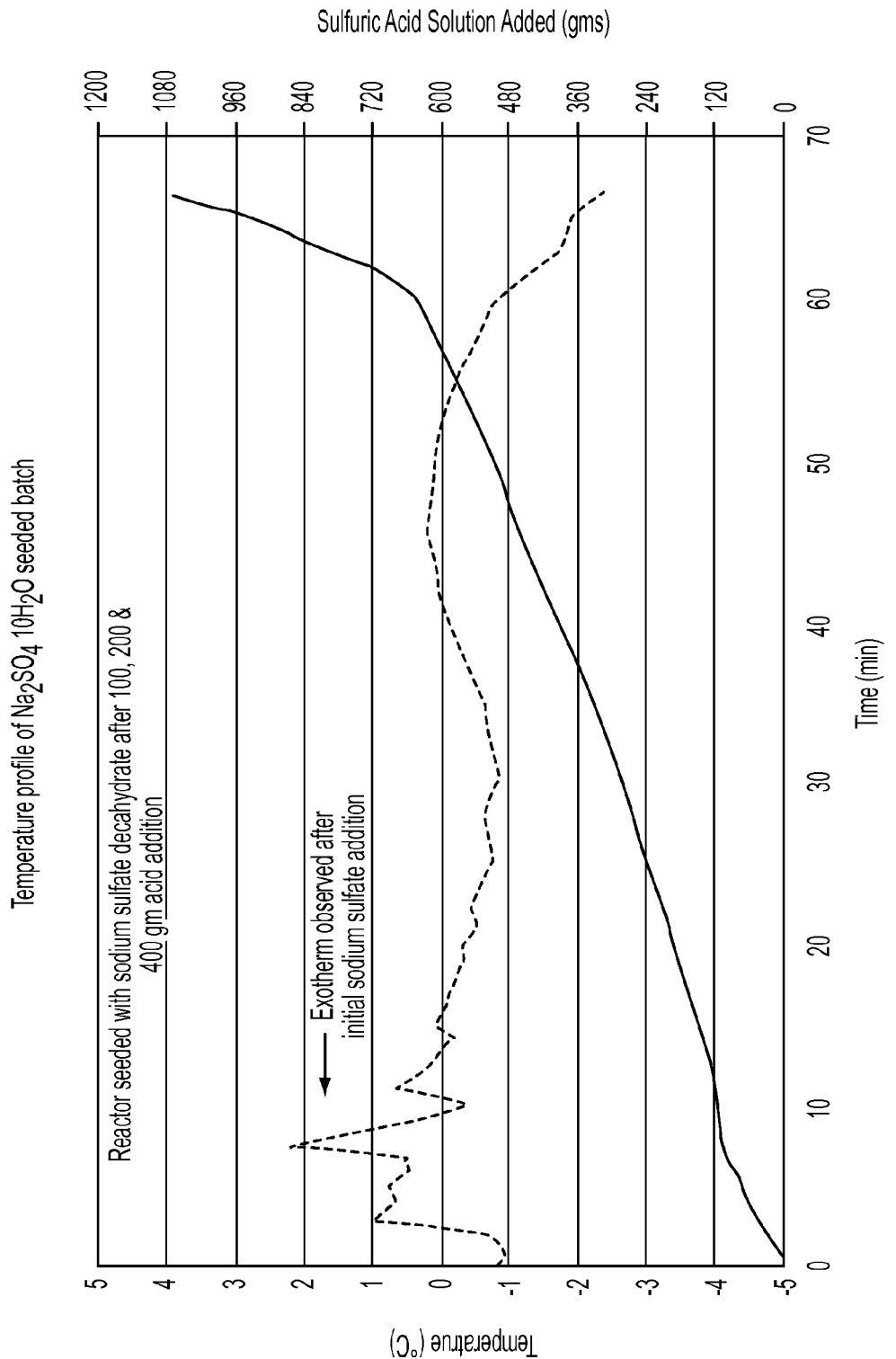
FIG. 2 illustrates the effect of sodium sulfate seeding on isoamyl nitrite synthesis.

Attention is directed to FIG. 1 which is a temperature profile of isoamyl nitrite synthesis with the uncontrolled exothermic sodium sulfate precipitation. In the absence of seeding, at approximately 10 to 20 minutes reaction time, the solution concentration of the sodium sulfate reaches supersaturation and an exothermic precipitation with the indicated temperature spike is observed. By contrast, attention is directed to FIG. 2, which illustrates the temperature profile in the presence of sodium sulfate seeding. More specifically, the temperature profile is shown for the reaction conducted with seeding after 10% of the sulfuric acid has been charged. The exotherm shown in FIG. 2 is significantly less than that shown in FIG. 1, demonstrating the ability of early seeding to maintain the temperature of the reaction between −5° C. and 2° C.

Figure 3:
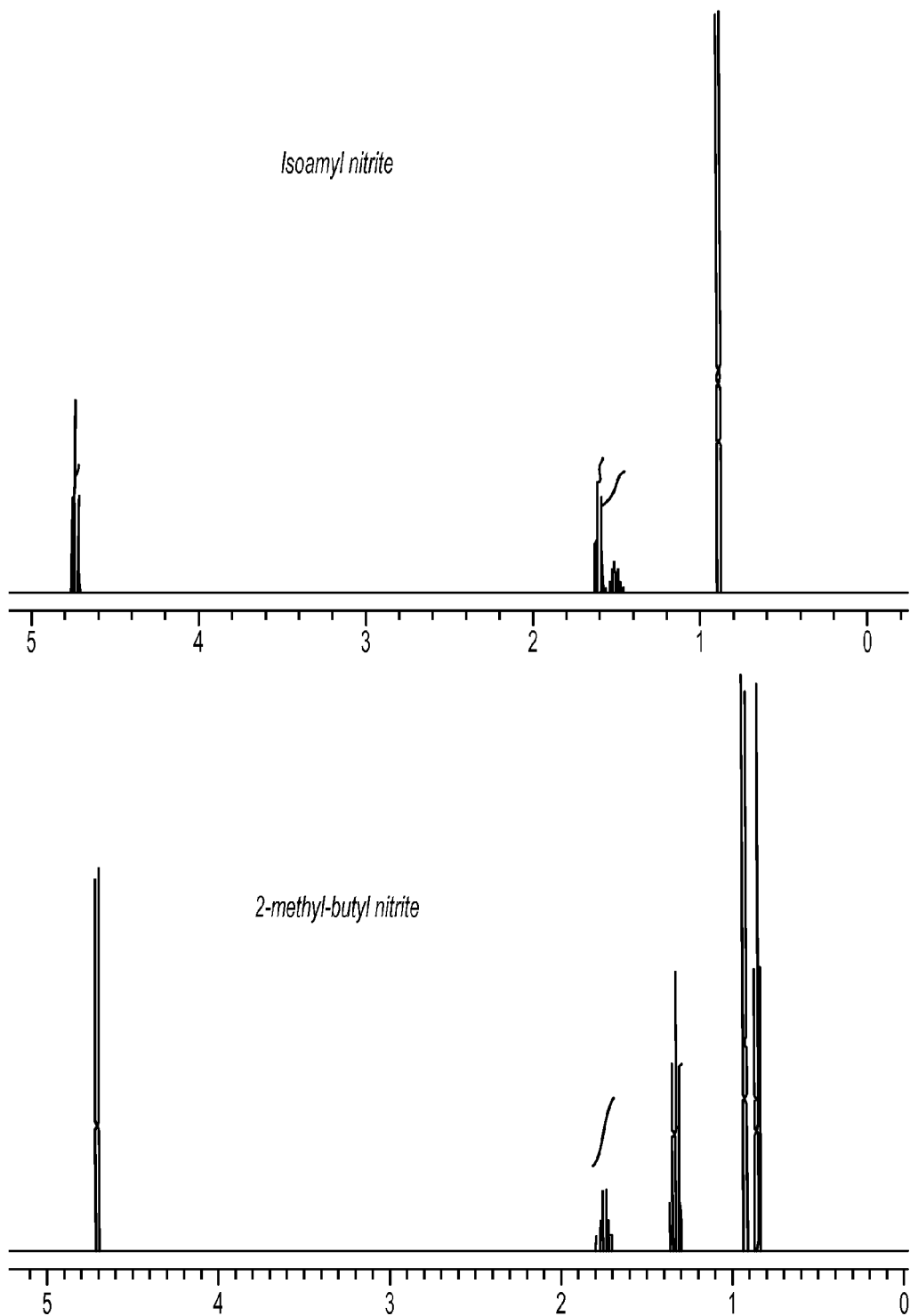
FIG. 3 illustrates the simulated NMR spectra for 3-methyl butyl nitrite (isoamyl nitrite) and the structural isomer 2-methylbutyl nitrite.
Figure 4:
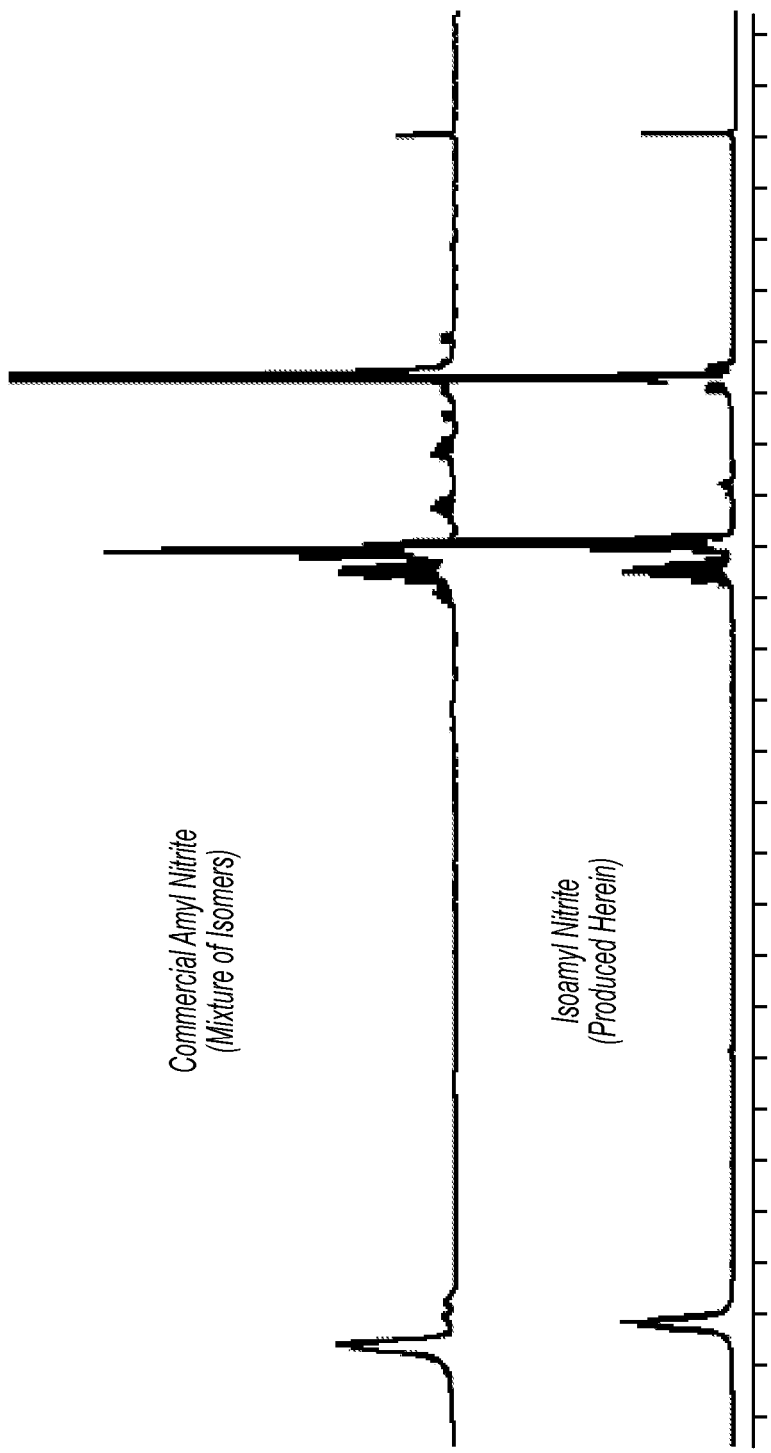
FIG. 4 illustrates the NMR spectra of commercially available amyl nitrite (top) and isoamyl nitrite produced by the disclosed method (bottom).

Attention is next directed to FIG. 3 which illustrates the simulated NMR spectra for isoamyl nitrite (3-methylbutyl nitrite) and 2-methyl butyl nitrite. FIG. 4 illustrates the actual NMR spectra of commercially available amyl nitrite (top) and isoamyl nitrite produced by the method identified herein (bottom). The NMR spectra of the prepared isoamyl nitrite has spectral features consistent with the calculated spectrum of 3-methylbutyl nitrite. The commercial sample has additional resonances. This includes a shoulder peak on the main methyl doublet. This shoulder is consistent with a methyl triplet. Additional apparent multiplet peaks appear in the CH and $CH_2$ region of unspecified multiplicity. The additional resonances near the broad alpha-nitrite peak suggest other isomers. The co-occurrence of these resonances is consistent with the presence of an additional isomer or isomers of amyl nitrite.

Preparation of Stabilized Isoamyl Nitrite (SIAN)

It has been found that isoamyl nitrite may be stabilized by mixture of 1.0-10.0% by weight with an epoxidized vegetable oil. Accordingly, the mixture may contain 1.0-10.0% by weight epoxidized vegetable oil and 99.0%-90.0% by weight isoamyl nitrite. Preferably, the level of epoxidized vegetable oil is 2.0%-6.0% by weight. Accordingly, the level of epoxidized vegetable oil may be, e.g., 2.0%, 3.0%, 4.0%, 5.0% or 6.0% by weight. A particular preferred level of epoxidized vegetable oil is from 3.0-5.0% by weight. Epoxidized vegetable oils are to be understood herein as naturally occurring triglycerides (triesters of glycerol and mixed unsaturated fatty acids) which include epoxide functionality. Preferred epoxidized vegetable oils include epoxidized linseed oil, epoxidized soybean oil, epoxidized safflower oil, epoxidized corn oil, epoxidized cottonseed oil, epoxidized rapeseed oil and epoxidized peanut oil. Theses oils are all epoxidized at unsaturated olefinic sites. The most preferred epoxidized vegetable oils are epoxidized soybean and epoxidized linseed oils, with epoxidized linseed oil the most preferred. Synthetic versions or refined versions of these epoxidized vegetable oils may also be employed The isoamyl nitrite that is stabilized via mixture with an epoxidized vegetable oil herein is preferably composed of the isomerically pure isoamyl nitrite noted herein. Such isomerically pure isoamyl nitrite may then be preferably combined and stabilized with epoxidized linseed oil, wherein the epoxidized linseed oil is present at a level of 2-6% by weight.

A stability study was conducted wherein isomerically pure isoamyl nitrite (90% by weight or more with other amyl nitrite isomers) was placed in glass ampoules with epoxidized linseed oil (ELSO) where the epoxidized linseed oil was present at 0.5% (wt.), 2.0% (wt.) and 4.0% (wt). At 40° C. there was some degradation of the samples containing 0% ELSO (unstabilized IAN), which showed a ~3% decrease relative to total impurities. The samples with 0.5% ELSO showed a ~1% decrease. There was no significant change in the 2% and 4% samples after 1 month at 40° C. Larger changes were observed at 50° C. including ~19% decrease for 0% ELSO samples and ~3% decrease for 0.5% ELSO samples relative to total impurities. With higher loadings of ELSO, the samples were more stable at 50° C. There was a 1% decrease for 2% ELSO, and no change for 4% ELSO. Based on these initial findings, 4% ELSO was selected to stabilize IAN to produce the formulations for initial preclinical studies. A summary of results is provided in Table 1, 2, and 3.

TABLE 1

IAN % With Varying ELSO In Sealed Ampoules, 1 Month Results (Area %)

| Amt ELSO (w/v) | T0 | 25° C. | 40° C. | 50° C. |
|---|---|---|---|---|
| 0% | 97.9 | 97.4 | 94.5 | 78.0 |
| 0.50% | 97.8 | 97.8 | 96.8 | 94.5 |
| 2.0% | 97.8 | 97.8 | 97.6 | 96.8 |
| 4.0% | 97.7 | 97.7 | 97.4 | 97.5 |

TABLE 2

Isoamyl alcohol, IAA Impurity In Sealed Ampoules At 1 Month (Area %)

| Amt ELSO (w/v) | T0 | 25° C. | 40° C. | 50° C. |
|---|---|---|---|---|
| 0% | 1.3 | 1.6 | 2.6 | 6.8 |
| 0.50% | 1.6 | 1.6 | 2.1 | 3.2 |
| 2.0% | 1.5 | 1.5 | 1.6 | 2.3 |
| 4.0% | 1.6 | 1.6 | 1.8 | 1.8 |

TABLE 3

Other Impurities In Sealed Ampoules At 1 Month (Area %)

| Amt ELSO (w/v) | T0 | 25° C. | 40° C. | 50° C. |
|---|---|---|---|---|
| Isovaleric Acid | | | | |
| 0% | ND | 0.16 | 0.66 | 2.23 |
| 0.50% | 0.01 | 0.02 | 0.12 | 0.39 |
| 2.0% | 0.03 | 0.03 | 0.04 | 0.07 |
| 4.0% | 0.04 | 0.04 | 0.05 | 0.04 |
| Isovalerate | | | | |
| 0% | 0.14 | 0.26 | 1.22 | 8.64 |
| 0.50% | 0.02 | 0.06 | 0.39 | 1.13 |
| 2.0% | 0.02 | 0.03 | 0.06 | 0.18 |
| 4.0% | 0.01 | 0.02 | 0.03 | 0.05 |

ND = not detected

As can be seen from the above tables, isoamyl nitrite may be combined with an epoxidized vegetable oil in which case the isoamyl nitrite maintains stability. More specifically, the present invention now provides a stabilized isoamyl nitrite formulation that maintains stability far better than in formulations with lower concentrations of epoxidized oil stabilizer.

The stabilized isoamyl nitrite herein was found to be further advantageously combined with petrolatum, a semi-solid mixture (at room temperature) of hydrocarbons that is insoluble in water. More specifically, petrolatum may comprise a hydrocarbon mixture of 16-32 carbon atoms having a melting point range of 35-55° C. at a specific gravity of 0.80-0.90. Such combination was found to increase the viscosity of the stabilized isoamyl nitrite formulation and to provide sustained release properties of the stabilized isoamyl reagent. Preferably, the isoamyl nitrite may be present at a level of at least 70% by weight, or in the range of 70.0-95.0% by weight. As noted above, the epoxidized vegetable oil is then present at 1.0-10.0% by weight with the balance comprising petrolatum. In addition, optionally, one may include fumed silica at a level of 0.1-20.0 wt. % to further increase the viscosity.

By way of example, mixtures of stabilized isoamyl nitrite (SIAN) can be combined with petrolatum according to the following general procedure:
1. Obtain the tare weight of a 40 mL I-Chem vial (with silicone septum cap and PTFE insert).
2. Weigh out the desired amount of petrolatum into the 40 mL I-Chem vial.
3. Add the desired amount of stabilized isoamyl nitrite (containing 4.0% by weight ELSO) to the I-Chem vial containing the petrolatum. Cap tightly.
4. Vortex until a relatively smooth thin gel of yellow color is observed.

Figure 5:
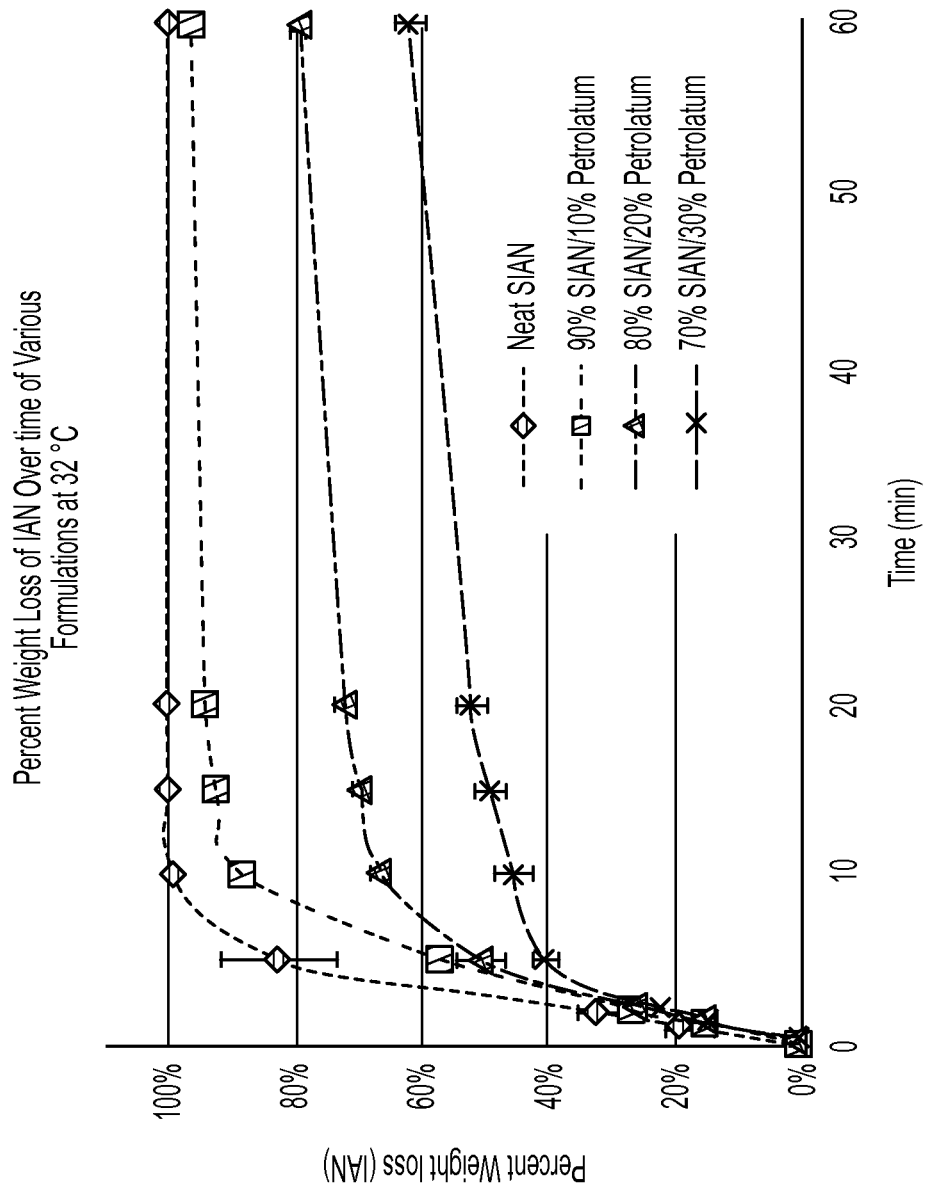
FIG. 5 illustrates gravimetric release profiles of isoamyl nitrite from formulations composed of isoamyl nitrite mixed with varying amounts of petrolatum.

Following the above, the following samples were prepared: (1) Neat SIAN; (2) 90% wt. SIAN/10% wt. Petrolatum; (3) 80% wt. SIAN/20% wt. Petrolatum; (4) 70% wt. SIAN/30% wt. Petrolatum. In all of these samples, the SIAN itself contained isomayl nitrite and 4.0% wt. epoxidized linseed oil. The gravimetric release profiles of the formulations at 32° C. are shown in FIG. 5. The weight of the samples decreases over time, indicating volatilization of the components. As the only volatile is isoamyl nitrite, the percent weight loss over time can be equated to volatilization of the active. As the amount of volatile active is increased from 70% SIAN to 90% SIAN (w/w), the release profiles indicate a more rapid release of the active. Error bars identify one standard deviation. As can be observed, a clear trend of relatively slower release over time is observed as the amount of petrolatum is increased.

It has also been found herein that as noted above, given the relatively low viscosity of isoamyl nitrite, one may increase viscosity by formation of nitrite functionalized derivatives of aliphatic polyethers. More specifically, one may again supply isoamyl nitrite and react with one or both of the terminal hydroxyl units of a hydroxyl-terminated polyethylene oxide according to the following general scheme:

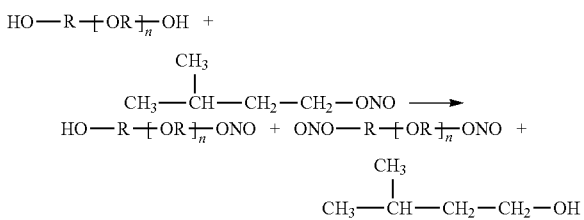

As can be seen, one may therefore selectively form nitrite functionality on either or both of the hydroxyl functional groups of the polyether polymer along with formation of isoamyl alcohol as the side-product. Accordingly, one may produce the indicated polyether type polymer with a single nitrite end group, two nitrite end groups, or a mixture of the two depending upon the reaction conditions or work-up and ensuing isolation of the reaction products. In addition, R herein is preferably an alkyl group comprising an ethyl, propyl, butyl or hexyl group and n has a value of 2-150. In addition, such formulations may include the addition of fumed silica, wherein the fumed silica is present at a level of 5-40% by weight and said nitrite functionalized polyether is present at a level of 95-60% by weight. A preferred form of fumed silica comprises Cabosil TS-530.

More preferably, the polyether noted herein comprises polyethylene glycol (PEG) and n has a value of 2-100. In such connection the PEG may have a MW of 400-600 g/mol. In addition, one may, e.g., combine 10-40% by weight of isoamyl nitrite with 90-60% by weight of the alcohol terminated polyether, such as PEG.

Figure 6:
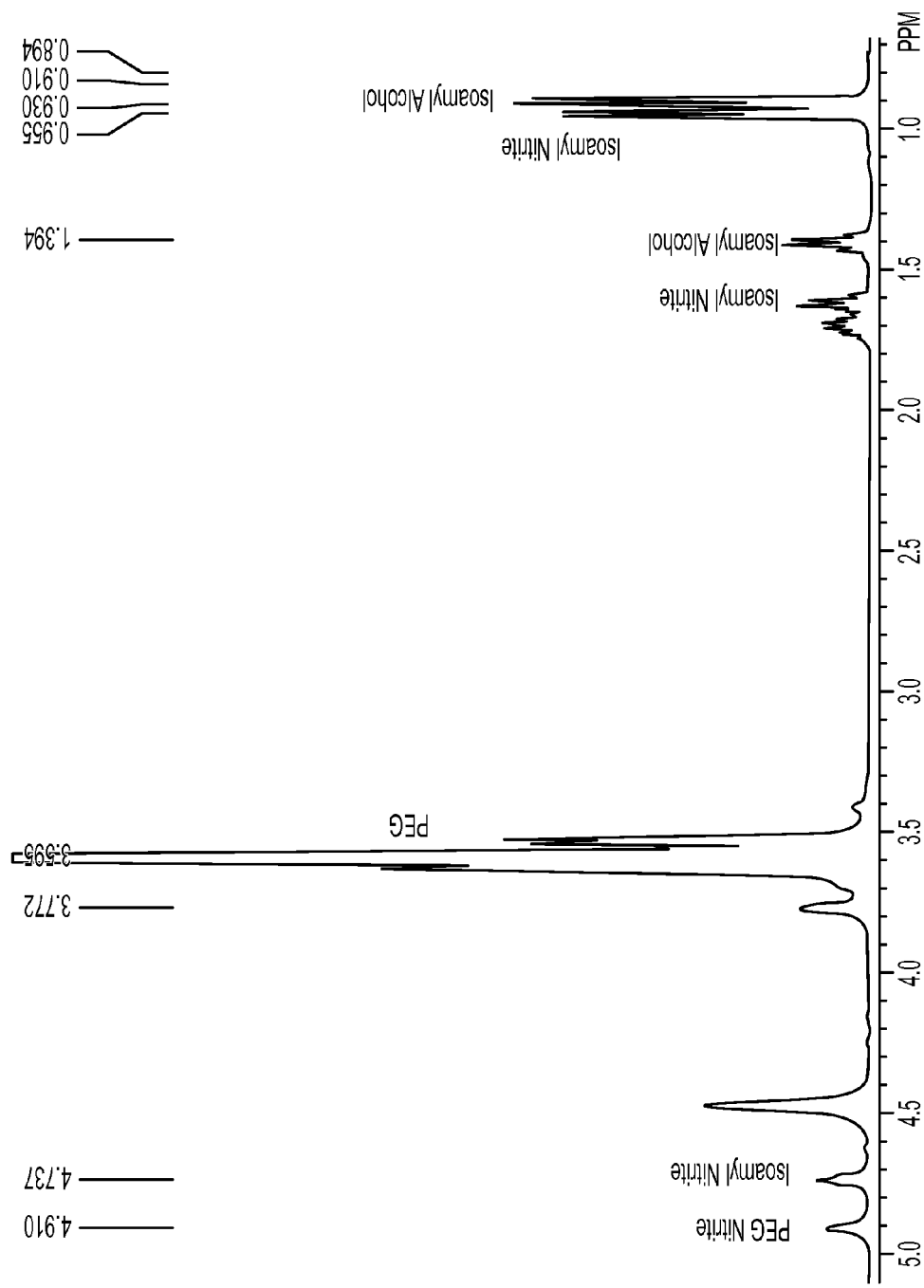
FIG. 6 illustrates NMR analysis of isoamyl nitrite and PEG nitrite.

By way of working example, 30.0% by weight of isoamyl nitrite was combined with 70.0% by weight PEG terminated with two hydroxyl groups. The sample was aged at room temperature for about 24 hours. Neither water nor acid nor base was added to facilitate the reaction. After aging, the sample may then be mixed with 10-20% by weight of Cabosil TS-530. Subsequent NMR analysis confirmed the presence of both isoamyl nitrite and PEG nitrite. See FIG. 6. Typically in the region of 0.9 ppm, isoamyl nitrite will indicate a doublet. The presence of the partner doublet suggests the presence of isoamyl alcohol. Another characteristic quartet of the alcohol appears at 1.4 ppm. Two peaks appear at 4.74 and 4.90 ppm. These peaks are consistent with the presence of isoamyl nitrite and also PEG nitrite. The isoamyl nitrite peak at 4.7 ppm shows evidence of a typical triplet characteristic that has been identified in isoamyl nitrite.

In still further embodiment the present invention relates to forming a mixture of isoamyl nitrite with a polysiloxane type polymer. The polysiloxane polymer may have the following formula:

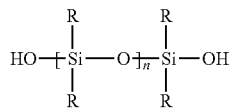

where the value of n provides a viscosity between 10-1000 cP and R is an alkyl group or aromatic group. Preferably, the isoamyl nitrite is present at a level of 10.0-99.9 wt. %, the polysiloxane polymer is present at a level of 0.1-90 wt. %. In addition, one may include fumed silica at a level of 0.1-20.0 wt. %. It is to be noted that there was no observed reaction between the isoamyl nitrite and the polysiloxane polymer as observed with the combination of isoamyl nitrite with the hydroxyl-terminated polyether described above. The mixture of isoamyl nitrite, polysiloxane polymer and fumed silica was observed to act as a controlled release formulation, slowing the evaporation of the isoamyl nitrite.

Efficacy of SIAN

A nasal instillation method was developed for delivery of the isoamyl nitrite formulations described herein. For viscous formulations, such as those containing petrolatum or polysiloxane, the method relies upon delivery of the isoamyl nitrite formulations herein (e.g. isoamyl nitrite stabilized with epoxidized linseed oil that is combined with petrolatum) utilizing a positive displacement micropipette equipped with a capillary piston tip. This allows the increased viscosity formulation to be accurately delivered to a given patient. For less viscous formulations, such as those containing only isoamyl nitrite and epoxidized vegetable oil, a blunt tipped needle can be used to deliver the formulation.

For example, for dosing in rats, preferably a 2 inch, 20 gauge, PTFE tipped needle is cut to a length of 7.0 mm past the end of the hub for intranasal dosing. This ensures that the dose volume is delivered to the approximate media of the nasal cavity and to preclude the SIAN dose from either evacuating through the nose or exiting through the trachea. The length of the needle is reduced to 7.0 mm to also reduce the potential irritation caused by the end of the tip contacting the olefactory epithilium. In addition, the 7.0 mm length is appropriate to place the distal tip of the dosing needle within the nasal terminates.

The method for nasal instillation of the SIAN formulations was observed to significantly increase the bioavailability of the active ingredient as shown indirectly by blood levels of methemoglobin (metHb) in rats which received the SIAN by nasal instillation. See Table 5. For comparison, normal metHb levels are below 1.0% and amyl nitrate inhalation studies in humans have found maximum levels of only 3.45-7.0%. By contrast, metHb levels achieved by nasal instillation of isoamyl nitrite in rats, as confirmed in Table 4, can reach 20.0% or greater.

TABLE 4

Blood Levels of metHB in Rats Receiving Isoamyl Nitrite by Nasal Installation

| Time Point (min) | Dose (µL) | Mean MetHb | Standard Error | No. of Samples |
|---|---|---|---|---|
| 2 | 50 | 12.1 | 2.3 | 3 |
| 2 | 75 | 18.1 | | 2 |
| 8 | 50 | 11.5 | 3.3 | 3 |
| 8 | 75 | 18.7 | 2.3 | 3 |
| 14 | 50 | 10.8 | 4.6 | 3 |
| 20 | 50 | 9.5 | 4.6 | 3 |
| 20 | 75 | 16.6 | 1.8 | 3 |
| 26 | 50 | 8.5 | 4.6 | 3 |
| 26 | 75 | 15.7 | 1.7 | 3 |
| 32 | 50 | 9.2 | | 2 |
| 32 | 75 | 13.8 | 1.4 | 3 |

Attention is next directed to Table 5, which shows the nasal instillation method as applied to an alternate formulation consisting of 80% SIAN (containing 4.0% epoxidized linseed oil and isoamyl nitrite) in combination with 20% petrolatum. As can be observed, the metHb levels achieved using the SIAN/petrolatum formulation at the same dosage levels can reach 40% and remain over 20% for more than 75 minutes.

TABLE 5

Methemoglobin As A Percentage of Total Hemoglobin (SIAN)

| Time Point | Animal ID | | | | | |
|---|---|---|---|---|---|---|
| | 201 | 202 | 203 | 204 | 205 | 206 |
| 2 | 30.5 | 26.1 | 36 | 33.3 | 22.2 | 28.5 |
| 8 | 34 | 29.7 | 40 | 35.9 | 23.4 | 30 |
| 15 | 35 | 28.5 | 40 | 35.5 | 22.1 | 30.6 |
| 21 | 32.8 | 26.8 | 39 | 34.5 | 20.9 | 29.6 |
| 30 | | | 37 | 32.7 | 17.7 | 28 |
| 42 | | | 34 | 29 | 14.5 | 24.7 |
| 48 | | | 32 | 26.8 | 13.4 | 23.1 |
| 60 | 24.9 | 17.1 | 28 | 23.6 | 10.7 | 19.5 |
| 75 | 21 | | 23 | 20.7 | | 15.4 |
| 90 | 18.2 | 10.7 | 19 | 16.9 | | 11.4 |

While a preferred embodiment of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

What is claimed is:
1. A composition comprising:
(a) isoamyl nitrite; and

(b) an epoxidized vegetable oil wherein said epoxidized oil is present at 1.0-10.0% by weight and said isoamyl nitrite is present at a level of 99.0-90.0% by weight.

2. The composition of claim 1 wherein said epoxidized vegetable oil is selected from epoxidized linseed oil, epoxidized soybean oil, epoxidized safflower oil, epoxidized corn oil, epoxidized cottonseed oil, epoxidized rapeseed oil and epoxidized peanut oil.

3. The composition of claim 1 wherein said epoxidized oil comprises epoxidized linseed oil and said epoxidized linseed oil is present at 2.0-6.0% by weight.

4. The composition of claim 1 wherein said isoamyl nitrite comprises only 3-methylbutyl nitrite.

5. The composition of claim 1 wherein said isoamyl nitrite comprises 3-methylbutyl nitrite in a mixture with other isomers of amyl nitrite wherein said 3-methylbutyl nitrite is present at a level of at least 90% by weight.

6. The composition of claim 1 wherein said isoamyl nitrite comprises only 3-methylbutyl nitrite and said epoxidized vegetable oil comprises epoxidized linseed oil present at a level of 3.0% to 5.0% by weight.

7. The composition of claim 1 wherein said composition further contains petrolatum.

8. The composition of claim 1 wherein said isoamyl nitrite is present at a level of 70.0-95.0% by weight, said epoxidized vegetable oil is present at a level of 1.0-10.0% by weight and the balance comprises a hydrocarbon mixture of 16-32 carbon atoms having a melting point range of 35-55° C. and a specific gravity of 0.80-0.90.

9. A composition comprising:
   (a) isoamyl nitrite;
   (b) a hydrocarbon mixture of 16-32 carbon atoms having a melting point range of 35-55° C. and a specific gravity of 0.80-0.90; and
   (c) epoxidized vegetable oil.

10. The composition of claim 9 further containing fumed silica present at a level of 0.1-20.0% by weight.

11. A method of treatment of cyanide poisoning, $H_2S$ poisoning or elevated blood pressure comprising instilling to an animal patient in need of such treatment a therapeutically effective amount of a composition comprising:
   (a) isoamyl nitrite; and
   (b) an epoxidized vegetable oil wherein said epoxidized oil is present at 1.0-10.0% by weight and said isoamyl nitrite is present at a level of 99.0-90.0% by weight.

12. The method of treatment of claim 11 wherein said epoxidized vegetable oil is selected from epoxidized linseed oil, epoxidized soybean oil, epoxidized sunflower oil, epoxidized cottonseed oil, epoxidized rapeseed oil and epoxidized peanut oil.

13. The method of claim 11 wherein said isoamyl nitrite comprises only 3-methylbutyl nitrite.

14. The method of claim 11 wherein said isoamyl nitrite is present at a level of 70.0-95.0% by weight, said epoxidized vegetable oil is present at a level of 1.0-10.0% by weight and the balance comprises a hydrocarbon mixture of 16-32 carbon atoms having a melting point range of 35-55° C. and a specific gravity of 0.80-0.90.

15. A method of treatment of cyanide poisoning, $H_2S$ poisoning or elevated blood pressure comprising instilling to an animal patient in need of such treatment a therapeutically effective amount of a composition comprising:
   (a) isoamyl nitrite;
   (b) a hydrocarbon mixture of 16-32 carbon atoms having a melting point range of 35-55° C. and a specific gravity of 0.80-0.90; and
   (c) epoxidized vegetable oil.

16. The method of claim 15 wherein said isoamyl nitrite comprises only 3-methylbutyl nitrite wherein said 3-methyl butyl nitrite is present at a level of 90% by weight or more.

17. The method of claim 15 further containing fumed silica at a level of 0.1-20.0% by weight.

* * * * *